(12) United States Patent
Hirawake et al.

(10) Patent No.: US 10,048,206 B2
(45) Date of Patent: Aug. 14, 2018

(54) FLUORESCENCE VIEWING DEVICE AND FLUORESCENCE VIEWING METHOD

(71) Applicant: HAMAMATSU PHOTONICS K.K., Hamamatsu-shi, Shizuoka (JP)

(72) Inventors: Kazumasa Hirawake, Hamamatsu (JP); Mitsuharu Miwa, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 194 days.

(21) Appl. No.: 14/780,680

(22) PCT Filed: Dec. 18, 2013

(86) PCT No.: PCT/JP2013/083927
§ 371 (c)(1),
(2) Date: Sep. 28, 2015

(87) PCT Pub. No.: WO2014/155869
PCT Pub. Date: Oct. 2, 2014

(65) Prior Publication Data
US 2016/0041098 A1    Feb. 11, 2016

(30) Foreign Application Priority Data

Mar. 29, 2013  (JP) ................. 2013-072782

(51) Int. Cl.
*G01N 21/64* (2006.01)
*A61B 5/00* (2006.01)
(Continued)

(52) U.S. Cl.
CPC ....... *G01N 21/6456* (2013.01); *A61B 5/0071* (2013.01); *G01N 21/6486* (2013.01);
(Continued)

(58) Field of Classification Search
CPC .................................... G01N 21/6456
See application file for complete search history.

(56) References Cited

U.S. PATENT DOCUMENTS

2008/0239070 A1    10/2008   Westwick et al.
2010/0245551 A1*    9/2010   Morita ............ A61B 1/00009
                                                    348/68
(Continued)

FOREIGN PATENT DOCUMENTS

CN    101424569    5/2009
CN    101634748    1/2010
(Continued)

OTHER PUBLICATIONS

Wilkinson, M. H. F., et al., "Automated and Manual Segmentation Techniques in Image Analysis of Microbes," Digital Image Analysis of Microbes, May 15, 1998, pp. 135-171, XP007920529.
(Continued)

*Primary Examiner* — Hugh H Maupin
(74) *Attorney, Agent, or Firm* — Drinker Biddle & Reath LLP

(57) ABSTRACT

A fluorescence viewing device is configured to take a difference between one of an image of a first frame and an image of a second frame output from an imaging device and the other of the first frame image and the second frame image stored in an image storage means, whereby clear observed images can be obtained without influence of background light. In the fluorescence viewing device, an exposure time of a fluorescence image acquisition period and an exposure time of a background image acquisition period are different from each other. Since ON/OFF durations of excitation light also become asymmetric according to the asymmetry of the exposure times, the device can reduce user's feeling of strangeness due to blinking of the excitation light.

10 Claims, 15 Drawing Sheets

(51) Int. Cl.
*A61B 1/00* (2006.01)
*A61B 1/04* (2006.01)
*A61B 1/06* (2006.01)

(52) U.S. Cl.
CPC ....... *A61B 1/00006* (2013.01); *A61B 1/00009* (2013.01); *A61B 1/043* (2013.01); *A61B 1/0638* (2013.01); *A61B 1/0646* (2013.01); *G01N 2201/061* (2013.01); *G01N 2201/062* (2013.01)

(56) References Cited

U.S. PATENT DOCUMENTS

| | | |
|---|---|---|
| 2012/0134603 A1 | 5/2012 | Pang et al. |
| 2013/0003922 A1 | 1/2013 | Watanabe |
| 2014/0184769 A1* | 7/2014 | Ishihara ............. A61B 1/00009 348/68 |

FOREIGN PATENT DOCUMENTS

| | | |
|---|---|---|
| CN | 101766476 | 7/2010 |
| EP | 1 067 375 | 1/2001 |
| JP | H07-155292 A | 6/1995 |
| JP | H10-151104 A | 6/1998 |
| JP | 2002-119464 | 4/2002 |
| JP | 2002-336187 | 11/2002 |
| JP | 2003-298952 | 10/2003 |
| JP | 2005-204905 | 8/2005 |
| JP | 3713347 | 11/2005 |
| JP | 2006-509573 A | 3/2006 |
| JP | 2006-349574 A | 12/2006 |
| JP | 2008-005754 | 1/2008 |
| JP | 2009-279171 | 12/2009 |
| JP | 2009-279172 | 12/2009 |
| JP | 2010-197251 | 9/2010 |
| JP | 2012-065898 | 4/2012 |
| JP | 2013-079841 A | 5/2013 |
| WO | WO 2013/024773 | 2/2013 |

OTHER PUBLICATIONS

English-language translation of International Preliminary Report on Patentability (IPRP) dated Oct. 8, 2015 that issued in WO Patent Application No. PCT/JP2013/083927.

* cited by examiner

Fig.13
(a) 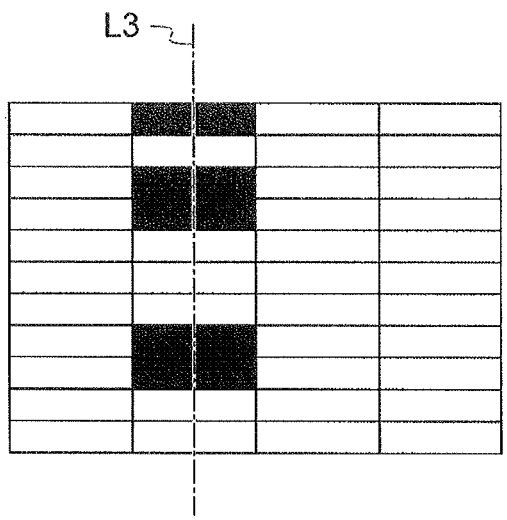
(b) 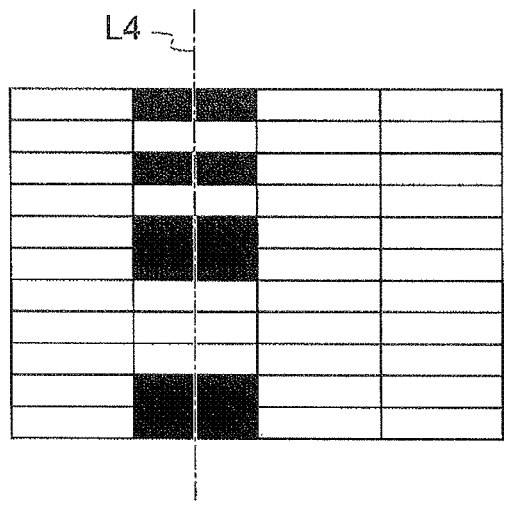

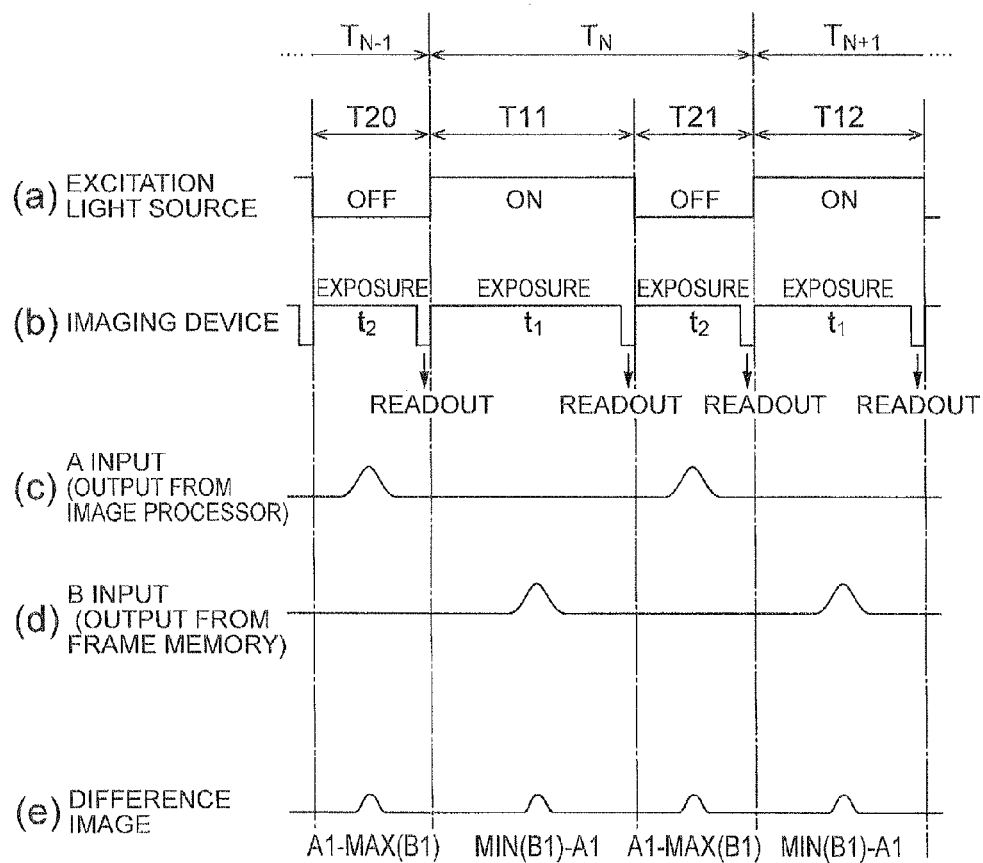

FLUORESCENCE VIEWING DEVICE AND FLUORESCENCE VIEWING METHOD

TECHNICAL FIELD

The present invention relates to a fluorescence viewing device and a fluorescence viewing method.

BACKGROUND ART

There are conventionally-known fluorescence viewing devices configured to supply and apply excitation light of a predetermined wavelength to an observed object and acquire an observed image of fluorescence generated in the observed object, by an imaging device. Such fluorescence viewing devices are used, for example, for identification of living tissue such as a lymph vessel or a lymph node in medical fields. When the fluorescence viewing is performed to observe temporal change of states of the observed object or the like, a method to be used is one to acquire images in a time series at a predetermined frame rate and observe a moving picture of the observed object (e.g., cf. Patent Literatures 1 and 2).

CITATION LIST

Patent Literatures

Patent Literature 1: Japanese Patent Application Laid-open Publication No. H10-151104
Patent Literature 2: Japanese Patent Application Laid-open Publication No. H07-155292

SUMMARY OF INVENTION

Technical Problem

Since the fluorescence viewing devices are configured to take observed images of weak fluorescence, there is a possibility of reduction in S/N ratios of the observed images if infrared wavelength components of room light, sunlight, or the like exit as background light. In order to eliminate influence of the background light, research has been conducted on a technique of taking a difference between an image with the supply of the excitation light ON (ON image) and an image with the supply of the excitation light OFF (OFF image). However, there are demands for enabling acquisition of the observed images with high S/N ratios in a short time while the influence of the background light is eliminated. We can expect improvement in S/N ratios by setting exposure times longer, but simple increase of the exposure times could lead to loss of smoothness of images (moving picture) of the object. There is another risk that a user viewing the observed images feels strangeness due to blinking of the excitation light, depending upon a relation between the exposure time of the ON image and the exposure time of the OFF image.

The present invention has been accomplished in order to solve the above problem and it is an object of the present invention to provide a fluorescence viewing device and a fluorescence viewing method capable of acquiring clear observed images with excellent visibility.

Solution to Problem

In order to solve the above problem, a fluorescence viewing device according to the present invention comprises: excitation light supply means for providing supply of excitation light for fluorescence observation to an observed object and is capable of implement ON/OFF switching of the supply of the excitation light; imaging means of a progressive readout type and for capturing an image of the observed object and alternately outputting a first frame image and a second frame image in a time series, as resultant image data of the observed object; image storage means for storing the first frame image or the second frame image output from the imaging means; and difference image generation means for generating a difference image by taking a difference between one of the first frame image and the second frame image output from the imaging means and the other of the first frame image and the second frame image stored in the image storage means, wherein the excitation light supply means switches the supply of the excitation light so that one of an image acquisition period of the first frame and an image acquisition period of the second frame by the imaging means is a fluorescence image acquisition period of a fluorescence image with the supply of the excitation light ON and so that the other is a background image acquisition period of a background image with the supply of the excitation light OFF, and wherein in the imaging means, an exposure time of the fluorescence image acquisition period and an exposure time of the background image acquisition period are different from each other.

In this fluorescence viewing device, the image data of the observed object is acquired in a time-series manner by progressive readout. The acquisition of the frame images is synchronized with the ON/OFF switching of the excitation light in such a manner that one of the image acquisition period of the first frame and the image acquisition period of the second frame is the fluorescence image acquisition period and that the other is the background image acquisition period. This operation allows clear observed images to be acquired without the influence of the background light, by taking the difference between one of the first frame image and the second frame image output from the imaging means and the other of the first frame image and the second frame image stored in the image storage means. In this fluorescence viewing device, the exposure time of the fluorescence image acquisition period and the exposure time of the background image acquisition period are different from each other. When the exposure time of the fluorescence image acquisition period and the exposure time of the background image acquisition period are made asymmetric in this manner, the observed images are obtained with good smoothness. Since ON/OFF durations of the excitation light also become asymmetric according to the asymmetry of the exposure times, it is feasible to reduce the user's feeling of strangeness due to the blinking of the excitation light.

Preferably, the fluorescence viewing device further comprises: image processing means for performing correction for a brightness of the fluorescence image and a brightness of the background image, based on a ratio of the exposure time of the fluorescence image acquisition period and the exposure time of the background image acquisition period. When the correction is made for the difference of brightnesses between the fluorescence image and the background image due to the difference of the exposure times, it is feasible to effectively remove the influence of the background light in taking the difference and to acquire clearer observed images.

Preferably, the image processing means executes a first correction to correct the brightness of the fluorescence image with use of a first correction value and a second correction to correct the brightness of the background image based on a second correction value, in synchronization with the switching of the supply of the excitation light. In this case, speed-up of processing is achieved because the correction for brightness is carried out in each image acquisition period.

Preferably, the excitation light supply means implements the switching of the supply of the excitation light so that the fluorescence image acquisition period is longer than the background image acquisition period. This configuration ensures the fluorescence intensity of the observed object at a more satisfactory level in the fluorescence image. Therefore, it becomes feasible to obtain clearer observed images.

Preferably, the exposure time of the background image acquisition period or the exposure time of the fluorescence image acquisition period is set less than 30 msec. In this case, since the fluorescence image acquisition period or the background image acquisition period is set not more than the temporal resolution of the retina in a human body, the user's feeling of strangeness due to blinking of the excitation light can be more effectively reduce. When the exposure time of the background image acquisition period is set less than 30 msec, the fluorescence image acquisition period becomes relatively longer and thus the fluorescence intensity of the observed object can be ensured at a more satisfactory level in the fluorescence image. Therefore, it becomes feasible to acquire clearer observed images.

Preferably, a total time of the fluorescence image acquisition period and the background image acquisition period is set equal to or less than 60 msec. This setting ensures the smoothness of the observed images at a higher level.

Preferably, the fluorescence viewing device further comprises: white light supply means for supplying white light to the observed object; imaging means for imaging a light figure of the observed object made by the white light supply means; and superimposed image generation means for superimposing the difference image generated by the difference image generation means, on a color image captured by the imaging means. When the color image of the observed object by the white supply means is superimposed on the difference image, the fluorescence is displayed on the color display image of the observed object and thus the visibility of the observed images is further enhanced.

Preferably, the fluorescence viewing device further comprises: filter process means for performing, with respect to the fluorescence image or the background image output from the image storage means to the difference image generation means and for a brightness of each pixel included in these images, a maximum filter process to define a maximum brightness among a plurality of pixels consisting of a target pixel and every pixel within a predetermined range near the target pixel, as a brightness of the target pixel, or, a minimum filter process to define a minimum brightness among a plurality of pixels consisting of a target pixel and every pixel within a predetermined range near the target pixel, as a brightness of the target pixel.

There are cases where a false difference image component is extracted, for example, at a boundary between a bright image portion and a dark image portion, in the difference image between the first frame image and the second frame image. Furthermore, the false difference image component can also be extracted with the observed object in motion. In such cases, the maximum filter process and the minimum filter process are applied to the background image and the fluorescence image, whereby the extraction of the false difference image component can be suppressed.

A fluorescence viewing method according to the present invention comprises: an excitation light supply step of providing supply of excitation light for fluorescence observation to an observed object and implementing ON/OFF switching of the supply of the excitation light; an imaging step of capturing an image of the observed object and performing progressive readout to alternately read a first frame image and a second frame image in a time series, as resultant image data of the observed object; an image storage step of storing the first frame image or the second frame image captured in the imaging step; and a difference image generation step of generating a difference image by taking a difference between one of the first frame image and the second frame image captured in the imaging step and the other of the first frame image and the second frame image stored in the image storage step, wherein the excitation light supply step comprises implementing the switching of the supply of the excitation light so that one of an image acquisition period of the first frame and an image acquisition period of the second frame in the imaging step is a fluorescence image acquisition period of a fluorescence image with the supply of the excitation light ON and so that the other is a background image acquisition period of a background image with the supply of the excitation light OFF, and wherein in the imaging step, an exposure time of the fluorescence image acquisition period and an exposure time of the background image acquisition period are made different from each other.

In this fluorescence viewing method, the image data of the observed object is acquired in a time-series manner by progressive readout. The acquisition of the frame images is synchronized with the ON/OFF switching of the excitation light in such a manner that one of the image acquisition period of the first frame and the image acquisition period of the second frame is the fluorescence image acquisition period and that the other is the background image acquisition period. This operation allows clear observed images to be acquired without the influence of the background light, by taking the difference between one of the first frame image and the second frame image acquired in the imaging step and the other of the first frame image and the second frame image stored in the image storage step. In this fluorescence viewing method, the exposure time of the fluorescence image acquisition period and the exposure time of the background image acquisition period are different from each other. When the exposure time of the fluorescence image acquisition period and the exposure time of the background image acquisition period are made asymmetric in this manner, the observed images are obtained with good smoothness. Since ON/OFF durations of the excitation light also become asymmetric according to the asymmetry of the exposure times, it is feasible to reduce the user's feeling of strangeness due to the blinking of the excitation light.

Advantageous Effect of Invention

The fluorescence viewing device and fluorescence viewing method according to the present invention have enabled the acquisition of clear observed images with excellent visibility.

BRIEF DESCRIPTION OF DRAWINGS

FIG. 13 is a drawing showing an example of images in the fluorescence viewing device shown in FIG. 8, in which (a) is a fluorescence image and (b) a background image.

FIG. 15 is a timing chart showing another modification example of the fluorescence viewing method to be executed in the fluorescence viewing device shown in FIG. 8.

DESCRIPTION OF EMBODIMENTS

The preferred embodiments of the fluorescence viewing device and fluorescence viewing method according to the present invention will be described below in detail with reference to the drawings.

First Embodiment

Figure 1:
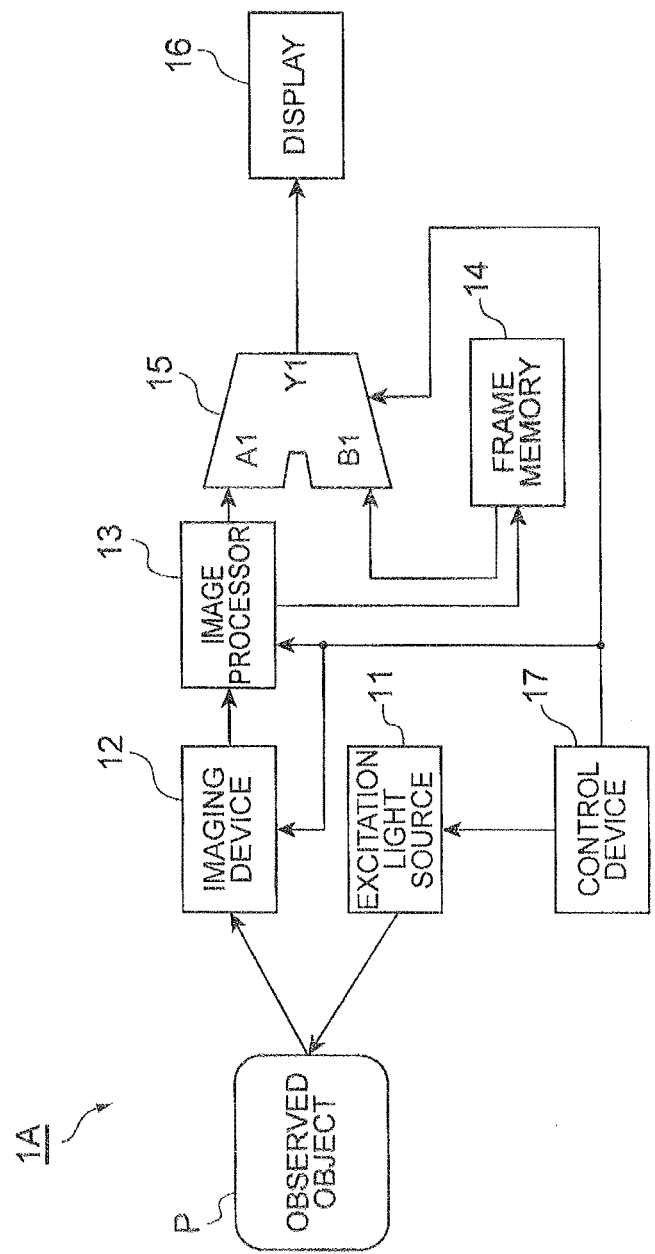
FIG. 1 is a block diagram showing a fluorescence viewing device according to the first embodiment of the present invention.

FIG. 1 is a block diagram showing the fluorescence viewing device according to the first embodiment of the present invention. The fluorescence viewing device 1A shown in the same drawing is configured to acquire observed images of an observed object P in a time series at a predetermined frame rate, thereby permitting a user to view a moving picture of the observed object P. The observed object P is, for example, living tissue, into which a fluorochrome such as indocyanine green is preliminarily introduced. The fluorescence viewing device 1A has, for example, an excitation light source 11, an imaging device 12, an image processing unit 13, a frame memory 14, a difference arithmetic unit 15, a display device 16, and a control device 17.

The excitation light source 11 is a device that provides supply of excitation light for fluorescence observation to the observed object P. The excitation light source 11 to be used herein is, for example, a near-infrared LED or SLD. The excitation light source 11 is configured to be able to implement ON/OFF switching of the supply of the excitation light under control of the control device 17. The excitation light source 11, more specifically, is controlled so as to implement the supply of the excitation light in synchronization with operation of the imaging device 12. The excitation light source 11 implements the supply of the excitation light in such a manner that one of an image acquisition period of a first frame and an image acquisition period of a second frame by the imaging device 12 is a fluorescence image acquisition period of a fluorescence image with the supply of the excitation light ON and that the other is a background image acquisition period of a background image with the supply of the excitation light OFF. It is noted herein that ON of the supply of the excitation light refers, for example, to a state in which the excitation light source 11 is switched on and OFF of the supply of the excitation light refers, for example, to a state in which the excitation light source 11 is switched off. OFF of the supply of the excitation light is not limited only to a case where the supply of the excitation light is completely stopped, but also includes a case where the intensity of the excitation light is made smaller than in the case of ON.

The imaging device 12 is a device that images a light figure from the observed object P under control of the control device 17. The imaging device 12 is a progressive imaging device that alternately outputs a first frame image and a second frame image in a time series, as image data of the observed object P. The progressive imaging device is a device that adopts progressive readout as a method for reading signals from an imaging element. The progressive readout is a method for progressively reading signals, without interlace scan during raster scanning, different from the interlace readout being one of the signal readout methods from the imaging element. The imaging device 12 has a spectroscopic means (not shown) such as a filter that cuts light in an excitation light wavelength region but transmits light in a fluorescence wavelength region, and images light from the spectroscopic means by means of an area image sensor such as a CCD image sensor or a CMOS image sensor.

In this imaging device 12, an image acquisition period of one frame consists of an exposure time and an image data readout time and, the exposure time of the fluorescence image acquisition period and the exposure time of the background image acquisition period are set different from each other. Therefore, the exposure time of the fluorescence image acquisition period and the exposure time of the background image acquisition period are not equal and are so set that either one of them is longer than the other. In the present embodiment, the exposure time of the fluorescence image acquisition period is set longer than the exposure time of the background image acquisition period and a ratio of them is, for example, about 5:1. It is noted that the fluorescence image acquisition period may be set shorter than the background image acquisition period.

The exposure time of the image acquisition period of the first frame and the exposure time of the image acquisition period of the second frame are set, for example, not more than 100 msec and set, preferably, equal to or less than 60 msec. In the progressive imaging device, generally, the frame rate is approximately 30 fps and the image acquisition period of one frame is approximately 33.3 msec. Therefore, since it is necessary to acquire images of two frames for acquisition of a difference image (described later) obtained by taking a difference between a fluorescence image and a background image, a time of about 60 msec is needed as a total time of the exposure time of the image acquisition period of the first frame and the exposure time of the image acquisition period of the second frame, and the frame rate of difference images is approximately 16.7 fps.

In general, the temporal resolution of the retina in a human body is in the range of about 50 msec to 100 msec and if the temporal resolution of the device is set over this range (or if the frame rate is set smaller than corresponding frame rates), there will be a risk of losing smoothness in display of difference images as a moving picture. Therefore, the smoothness of difference images can be guaranteed when the image acquisition period of the first frame and the image acquisition period of the second frame are set not more than 100 msec and preferably not more than 60 msec.

The exposure time of the fluorescence image acquisition period is set not less than 30 msec, while the exposure time of the background image acquisition period is set not more than 30 msec. As the sufficient fluorescence image acquisition period is secured in this manner, the fluorescence image can be acquired as a clear image. On the other hand, even if the exposure time of the background image acquisition period is shorter than the exposure time of the fluorescence image acquisition period, there will arise no problem in acquisition of the background image; even about 10 msec is sufficient. The readout time is usually approximately from several ten psec to several hundred psec, which is extremely smaller than the exposure times. Therefore, a satisfactorily clear fluorescence image can be acquired by adjusting the setting of the exposure times.

Furthermore, it is preferred that either one of the exposure time of the fluorescence image acquisition period and the exposure time of the background image acquisition period be set not more than the temporal resolution of the retina in a human body. In the present embodiment, the ON/OFF switching of the excitation light from the excitation light source 11 is also implemented in conjunction with changeover between the fluorescence image acquisition period and the background image acquisition period. Namely, the control device 17 controls the excitation light source 11 so that the excitation light is ON during the exposure time of the fluorescence image acquisition period and the control device 17 controls the excitation light source 11 so that the excitation light is OFF during the exposure time of the background image acquisition period (or so that the intensity of the excitation light is made smaller). The temporal resolution of the retina, though different with each person, is approximately in the range of 50 msec to 100 msec. Therefore, when either one of the exposure time of the fluorescence image acquisition period and the exposure time of the background image acquisition period is less than 30 msec, it is feasible to effectively reduce the feeling of strangeness due to the blinking of the excitation light, for the user viewing the observed images.

The image processing unit 13 is a part that adjusts brightnesses of image data taken by the imaging device 12 on the basis of control by the control device 17. The image processing unit 13 corrects the brightness of the fluorescence image and the brightness of the background image, based on the ratio of the exposure time of the fluorescence image acquisition period and the exposure time of the background image acquisition period. The image processing unit 13 implements switching of correction values based on the ratio of the exposure time of the fluorescence image acquisition period and the exposure time of the background image acquisition period, in conjunction with changeover of input images, to correct the brightness of the fluorescence image and the brightness of the background image. Namely, the image processing unit 13 switches the correction values from one to the other in conjunction with the ON/OFF switching of the excitation light from the excitation light source 11.

When the exposure time of the fluorescence image acquisition period is set longer than the exposure time of the background image acquisition period as in the present embodiment, the image processing unit 13 performs the correction as follows: for example, when the exposure time of the fluorescence image acquisition period is $t_1$ and the exposure time of the background image acquisition period is $t_2$, the correction with input of the fluorescence image is performed so as to maintain the brightness of the fluorescence image without change (first correction value), while the correction with input of the background image is performed so as to multiply the brightness of the background image by $(t_1/t_2)$ (second correction value). Signals concerning the changeover of input images are fed from the control device 17 to the image processing unit 13.

As the correction is made for the difference of brightnesses between the fluorescence image and the background image due to the difference of the exposure times in this manner, influence of background light is effectively removed in taking the difference and the observed images can be acquired as clearer images. In the case where the brightness input into the image processing unit 13 is output as maintained without change, we can also consider this case as correction with the correction value of one. Furthermore, the image processing unit 13 may be configured to perform such correction that the brightness of the background image is maintained without change (second correction value) while the brightness of the fluorescence image is multiplied by $(t_2/t_1)$ (first correction value).

The frame memory 14 is a part that stores the first frame image or the second frame image output from the imaging device 12. The frame memory 14 stores the fluorescence image or the background image corrected by the image processing unit 13.

The difference arithmetic unit 15 is a part that generates a difference image by taking a difference between one of the first frame image and the second frame image output from the imaging device 12 and the other of the first frame image and the second frame image stored in the image storage means. More specifically, the difference arithmetic unit 15 receives one of the fluorescence image or the background image output from the image processing unit 13 and the other of the fluorescence image and the background image stored in the frame memory 14, and performs an operation to calculate the difference between them.

The difference arithmetic unit to be used herein is, for example, an arithmetic logical device (ALU: Arithmetic Logic Unit). An output of the image processing unit 13 is output to an A1 input terminal of the difference arithmetic unit 15 and an output of the frame memory 14 is connected to a B1 input terminal of the difference arithmetic unit 15. A difference image as the result of the operation is output from a Y1 output terminal of the difference arithmetic unit 15. In the difference operation, the output is zero if the operation result is negative.

The display device 16 is a device that displays the difference image generated by the difference arithmetic unit 15. The fluorescence viewing device 1A may be provided with an image output device except for the display device

16, or may be configured to output the image data of the resultant difference image to the outside, without provision of the display device 16.

Figure 2:
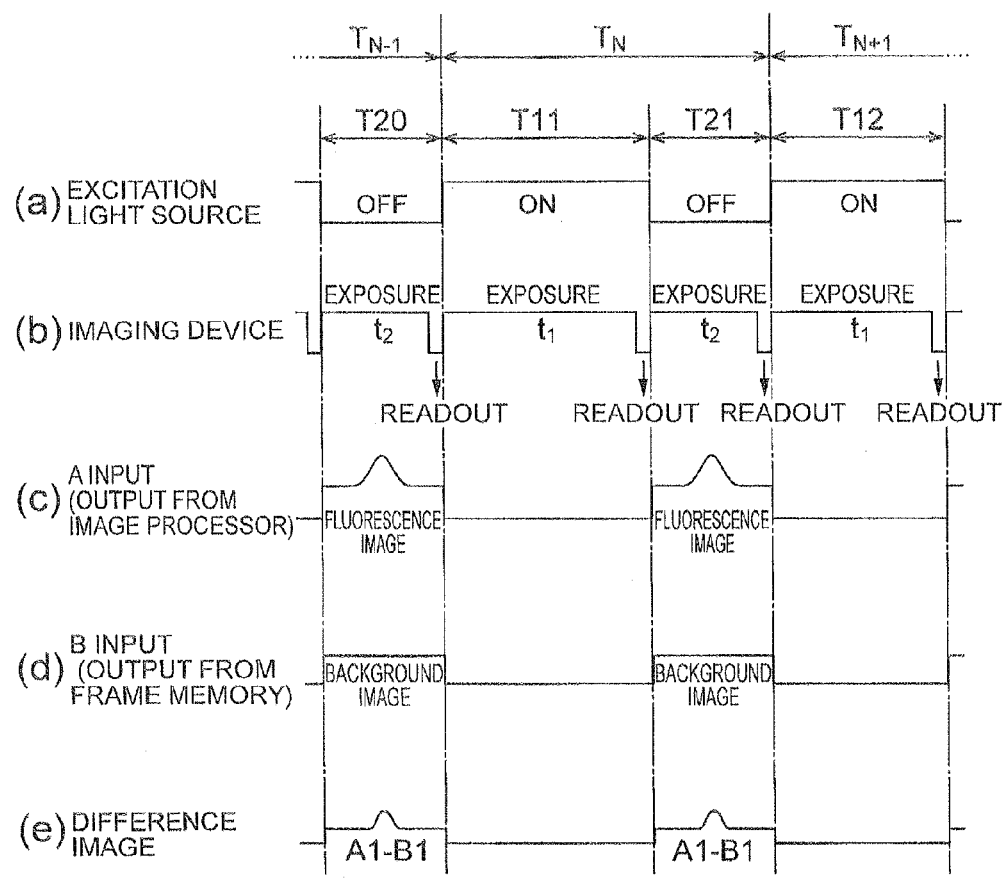
FIG. 2 is a timing chart showing a fluorescence viewing method to be executed in the fluorescence viewing device shown in FIG. 1.

FIG. 2 is a timing chart showing a fluorescence viewing method to be executed in the fluorescence viewing device shown in FIG. 1. In this timing chart, (a) indicates ON/OFF of the excitation light source, (b) the image acquisition period of the first frame and the image acquisition period of the second frame in the imaging device, (c) the A1 input of the difference arithmetic unit, (d) the B1 input of the difference arithmetic unit, and (e) the generated difference image.

In the timing chart of FIG. 2, a frame acquisition period $T_N$ for acquisition of a difference image of one frame consists of an image acquisition period T11 of the first frame and an image acquisition period T21 of the second frame. In the example of the same drawing, the image acquisition period T1 is the fluorescence image acquisition period, in which the supply of the excitation light is ON. The image acquisition period T21 is the background image acquisition period, in which the supply of the excitation light is OFF.

As described above, the exposure time $t_1$ of the fluorescence image acquisition period is set so as to be longer than the exposure time $t_2$ of the background image acquisition period. In the example of FIG. 2, the exposure time $t_1$ is, for example, 50 msec and the exposure time $t_2$, for example, 10 msec. Therefore, the ON time of the excitation light in the image acquisition period T11 is also about 50 msec and the OFF time of the excitation light in the image acquisition period T21 is also about 10 msec. It is noted that each of these ON time and OFF time of the excitation light includes the readout time of the imaging device.

The fluorescence image acquired in the image acquisition period T11 is fed through the brightness correction based on the first correction value in the image processing unit 13, to the A1 input terminal of the difference arithmetic unit 15 in the image acquisition period T21. The background image acquired in the image acquisition period T20 of the immediately preceding frame acquisition period $T_{N-1}$ is fed through the brightness correction based on the second correction value in the image processing unit 13, to the frame memory 14 in the image acquisition period T11 and is then fed to the B1 input terminal of the difference arithmetic unit 15 in the image acquisition period T21. Then, an A1−B1 operation to calculate the difference between the fluorescence image at the A1 input and the background image at the B1 input is executed in the image acquisition period T21 to generate the difference image as extraction of fluorescence.

The supply of the excitation light, the imaging by the imaging device 12, the brightness correction in the image processing unit 13, and the generation of the difference image in the difference arithmetic unit 15 are repetitively executed in the image acquisition period of the first frame and the image acquisition period of the second frame in each of frame acquisition periods. This operation causes the generated difference images to be output in a time series from the Y1 output to the display device 16, whereby the observed images of the observed object P are displayed as a moving picture.

As described above, the fluorescence viewing device 1A acquires the image data of the observed object P in a time series by progressive readout. Furthermore, the acquisition of frame images and ON/OFF of the excitation light are synchronized so that one of the image acquisition period of the first frame and the image acquisition period of the second frame is the fluorescence image acquisition period and the other is the background image acquisition period. This setting allows the device to acquire a clear observed image without influence of background light, by taking the difference between one of the first frame image and the second frame image output from the imaging device 12 and the other of the image of the first image and the second frame image stored in the image storage means.

In this fluorescence viewing device 1A, the exposure time of the fluorescence image acquisition period and the exposure time of the background image acquisition period are different from each other. When the exposure time of the fluorescence image acquisition period and the exposure time of the background image acquisition period are made asymmetric in this manner, the observed images are obtained with good smoothness. Since the ON/OFF durations of the excitation light are also asymmetric according to the asymmetry of the exposure times, it is feasible to reduce the user's feeling of strangeness due to the blinking of the excitation light.

In this fluorescence viewing device 1A, the brightness of the fluorescence image and the brightness of the background image are corrected based on the ratio of the exposure time of the fluorescence image acquisition period and the exposure time of the background image acquisition period. By performing the correction for the difference of brightnesses between the fluorescence image and the background image due to the difference of the exposure times, the influence of the background light is effectively removed in taking the difference and the observed images are acquired as clearer images.

In the present embodiment, the supply of the excitation light is switched so that the fluorescence image acquisition period is longer than the background image acquisition period and, in conjunction therewith, the exposure time of the fluorescence image acquisition period is set longer than the exposure time of the background image acquisition period. This allows the fluorescence image to be acquired in the sufficient exposure time, whereby the fluorescence intensity is secured at a more satisfactory level in the fluorescence image. Therefore, it becomes feasible to obtain clearer observed images.

Figure 3:
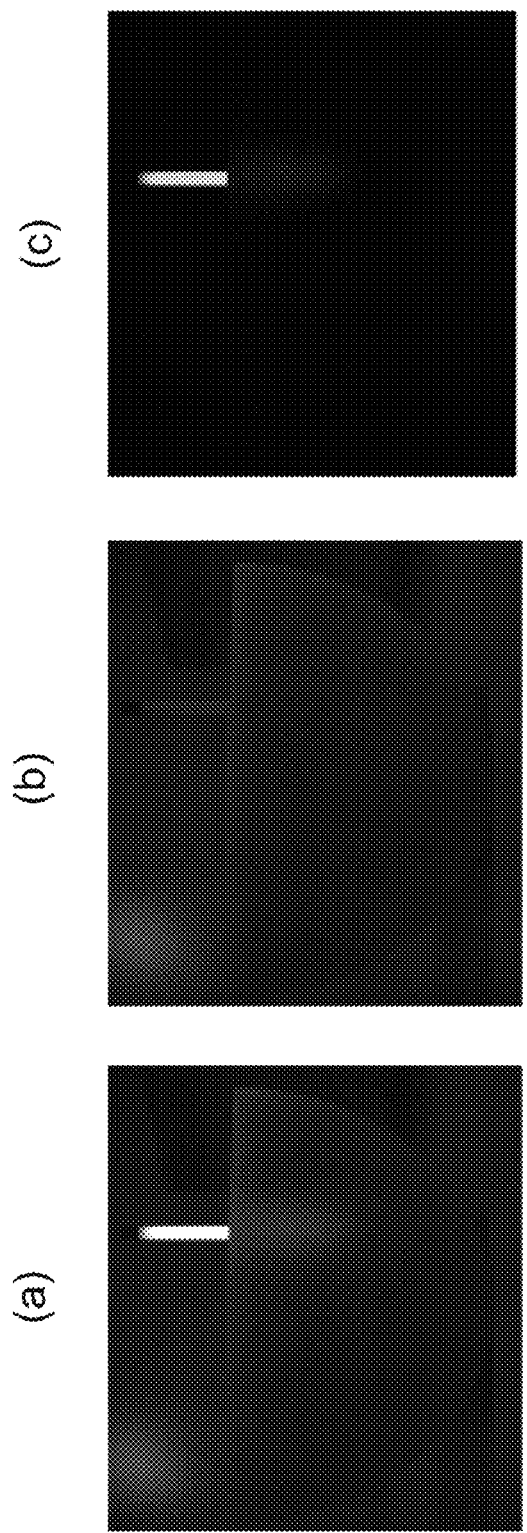
FIG. 3 is a drawing showing an example of images in Comparative Example, in which (a) is a fluorescence image, (b) a background image, and (c) a difference image.
Figure 4:
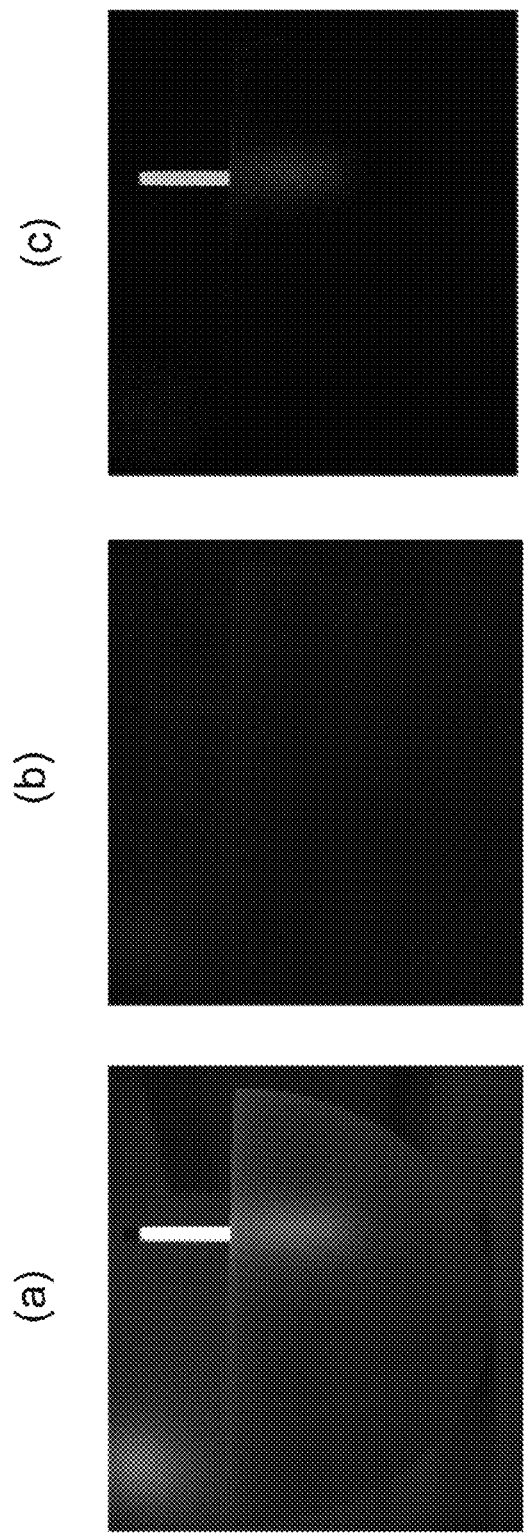
FIG. 4 is a drawing showing an example of images in Example, in which (a) is a fluorescence image, (b) a background image, and (c) a difference image.

FIG. 3 is a drawing showing an example of images in Comparative Example, in which (a) is a fluorescence image, (b) a background image, and (c) a difference image. FIG. 4 is a drawing showing an example of images in Example, in which (a) is a fluorescence image, (b) a background image, and (c) a difference image.

In Comparative Example shown in FIG. 3, the ratio of the exposure time of the fluorescence image acquisition period and the exposure time of the background image acquisition period is set to 1:1 (30 msec:30 msec). On the other hand, in Example shown in FIG. 4, while the frame acquisition periods are set to the same as in Comparative Example, the ratio of the exposure time of the fluorescence image acquisition period and the exposure time of the background image acquisition period is set to 5:1 (50 msec:10 msec), the brightness of the background image is corrected by multiplication of five times, and then the difference image thereof from the fluorescence image is taken. It can be confirmed by this result that the influence of background light is effectively removed and the observed images can also be acquired as clearer images by the fluorescence viewing method of the fluorescence viewing device 1A in which the exposure time of the fluorescence image acquisition period and the exposure time of the background image acquisition period are set different.

Second Embodiment

Figure 5:
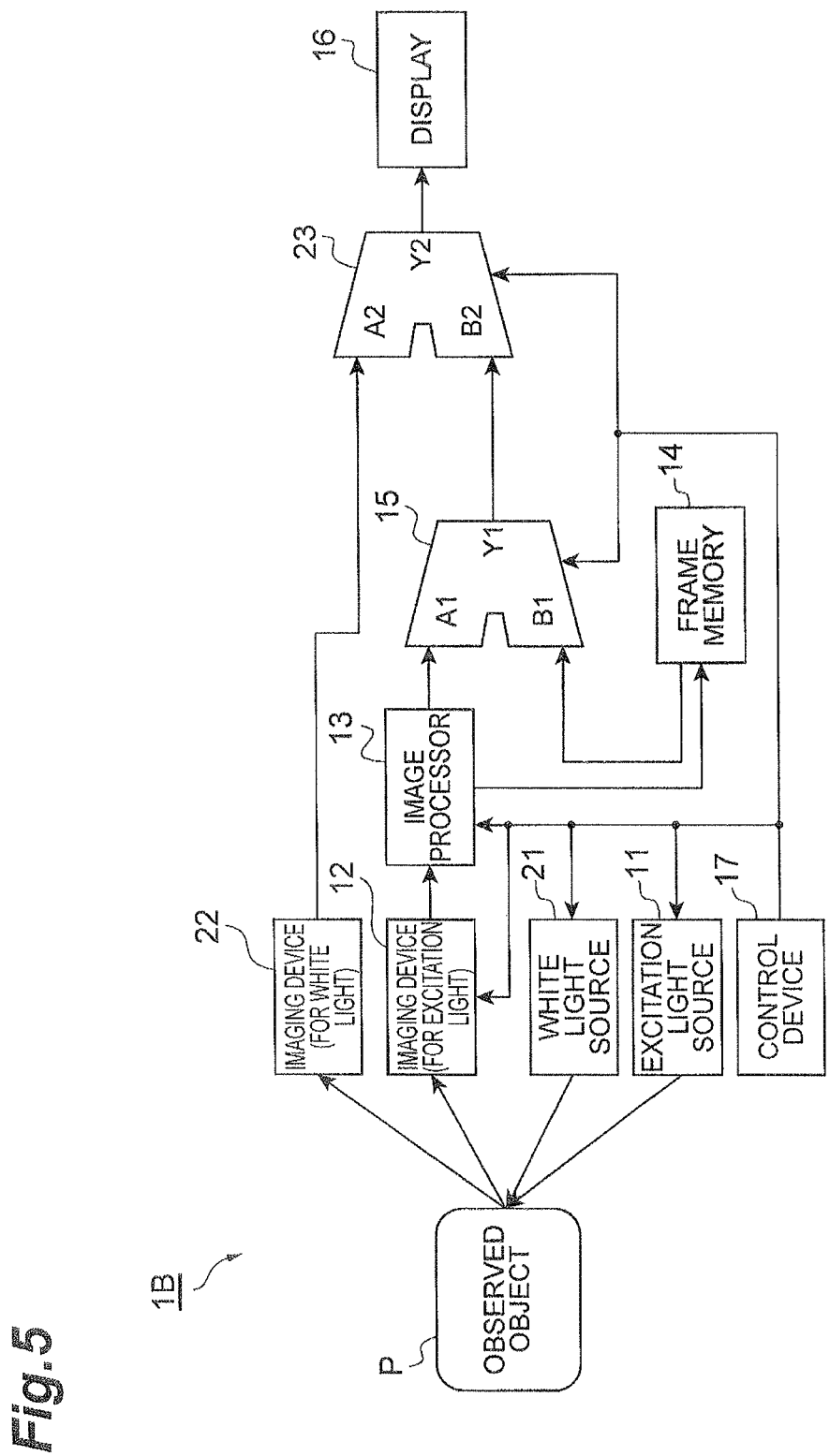
FIG. 5 is a block diagram showing the fluorescence viewing device according to the second embodiment of the present invention.

FIG. 5 is a block diagram showing the fluorescence viewing device according to the second embodiment of the present invention. As shown in the same drawing, the fluorescence viewing device 1B of the second embodiment is different from the first embodiment in that the fluorescence viewing device 1B further has a white light source 21 for supplying white light to the observed object P, an imaging device 22 for imaging a light figure of the observed object P made by the white light source 21, and a superimposition arithmetic unit 23 for superimposing a color image taken by the imaging device 22, on the difference image generated by the difference arithmetic unit 15.

The white light source 21 is, for example, an illumination light source such as a white LED. The imaging device 22 has a spectroscopic means (not shown) such as a filter for transmitting light in the visible region and images light from the spectroscopic means by an area sensor such as a CCD image sensor or a CMOS image sensor to take a color image of the observed object P. The imaging device 12 for the excitation light source and the imaging device 22 for the white light source are preferably arranged so as to image coaxially dispersed light figures. In this case, the area image sensors may be arranged so as to be able to image light figures dispersed into a plurality of optical paths by the spectroscopic means (not shown) such as a prism or a beam splitter, for example. Alternatively, the device may be configured so that the light figures dispersed into the plurality of optical paths are received by one area image sensor.

The superimposition arithmetic unit 23 is an arithmetic logical device similar to the difference arithmetic unit 15. The color image data acquired by the imaging device 22 is fed to an A2 input terminal of the superimposition arithmetic unit 23 and the difference image data from the Y1 output terminal of the difference arithmetic unit 15 is fed to a B2 input terminal of the superimposition arithmetic unit 23. Then the superimposition arithmetic unit 23 superimposes the color image on the difference image data and outputs the resultant image from a Y2 output terminal to the display device 16.

Figure 6:
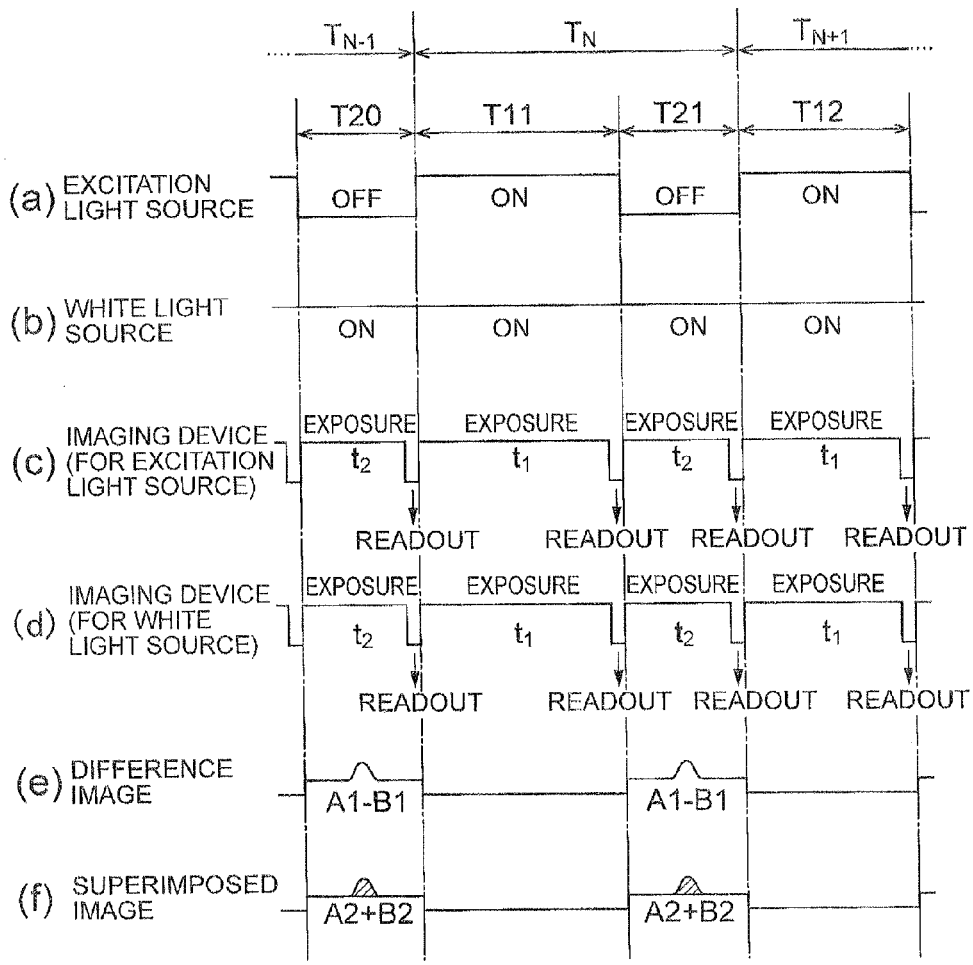
FIG. 6 is a timing chart showing the fluorescence viewing method to be executed in the fluorescence viewing device shown in FIG. 5.

FIG. 6 is a timing chart showing the fluorescence viewing method to be executed in the fluorescence viewing device shown in FIG. 5. In this timing chart, (a) shows ON/OFF of the excitation light source, (b) ON/OFF of the white light source, (c) the image acquisition period of the first frame and the image acquisition period of the second frame in the imaging device for the excitation light source, (d) the image acquisition period of the first frame and the image acquisition period of the second frame in the imaging device for the white light source, (e) the generated difference image, and (f) the generated superimposed image.

In the timing chart of FIG. 6, the operations of the excitation light source 11 and the imaging device 12 for the excitation light source 11, and the generated difference image are the same as those in the case of FIG. 2. The white light source 21 is continuously kept ON in both of the fluorescence image acquisition period and the background image acquisition period, and the imaging device 22 for the white light source 11 performs exposure and readout of the color image in synchronization with the operation of the imaging device 12 for the excitation light source 11. In the image acquisition period T21, an A2+B2 operation to implement the superimposition of the color image at the A2 input and the difference image at the B2 input is executed, thereby generating the observed image as superimposition of the color image and the difference image.

In this fluorescence viewing device 1B as described above, the exposure time of the fluorescence image acquisition period and the exposure time of the background image acquisition period are also different from each other. When the exposure time of the fluorescence image acquisition period and the exposure time of the background image acquisition period are made asymmetric in this manner, the observed images are obtained with good smoothness. Since the ON/OFF durations of the excitation light are also asymmetric according to the asymmetry of the exposure times, it is feasible to reduce the user's feeling of strangeness due to the blinking of the excitation light. Since the fluorescence is displayed on the color display image of the observed object P by the superimposition of the color image of the observed object P made by the white light source 21 on the difference image, the visibility of the observed images can be further enhanced.

Figure 7:
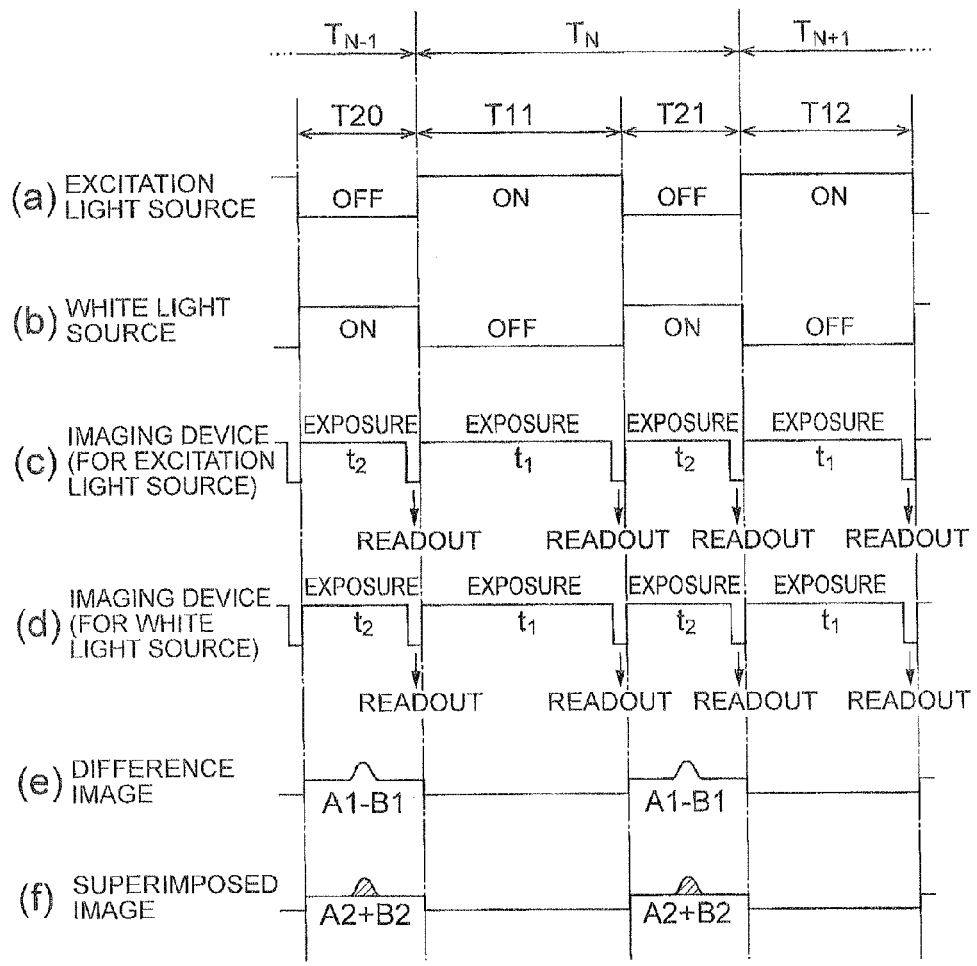
FIG. 7 is a timing chart showing a modification example of the fluorescence viewing method to be executed in the fluorescence viewing device shown in FIG. 5.

Since in the timing chart of FIG. 6 the white light source 21 is always kept ON (lighting), even if the wavelength region of white light from the white light source 21 has an overlap (including a partial overlap) with the wavelength region of the excitation light from the excitation light source 11, the fluorescence image and the background image both include fluorescence excited by the white light and thus influence thereof is eliminated from the difference image. It is noted, however, that, as shown in FIG. 7, the ON/OFF switching of the white light source 21 may be set inverse to the ON/OFF switching of the excitation light source 11. Even in the case of the timing chart shown in FIG. 6, if a spectroscopic means (not shown) such as a band-pass filter is located on the optical path of the white light from the white light source 21 so as to cut the light in the wavelength region of the excitation light out of the wavelength region of the white light from the white light source 21, the fluorescence image can be prevented from being affected by the while light source, whereby the colored observed images can be suitably obtained.

Third Embodiment

Figure 8:
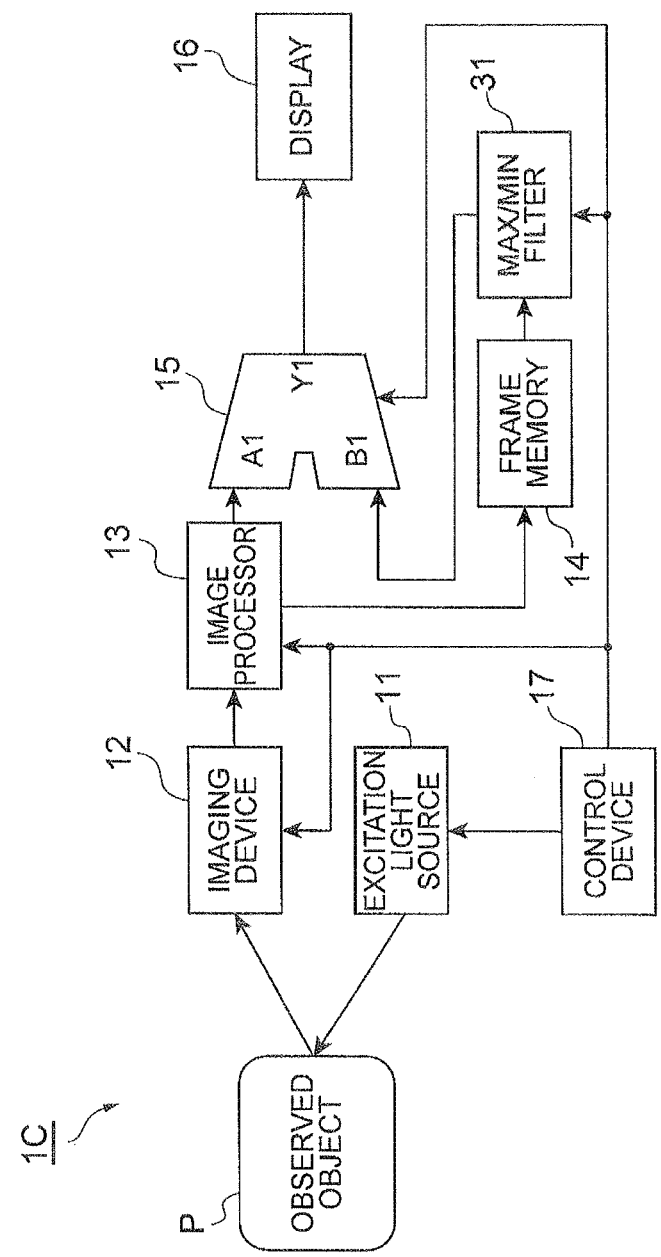
FIG. 8 is a block diagram showing the fluorescence viewing device according to the third embodiment of the present invention.

FIG. 8 is a block diagram showing the fluorescence viewing device according to the third embodiment of the present invention. As shown in the same drawing, the fluorescence viewing device 1C of the third embodiment is different from the first embodiment in that the fluorescence viewing device 1C further has a MAX/MIN filter 31 as a subsequent stage to the frame memory 14.

This MAX/MIN filter 31 is a filter that preforms, for the fluorescence image or the background image output from the frame memory 14 to the difference arithmetic unit 15 and for a brightness of each pixel included in these images, a maximum filter process to define a maximum brightness among a plurality of pixels consisting of a target pixel and every pixel in a predetermined range near the target pixel, as a brightness of the target pixel, or, a minimum filter process to define a minimum brightness among a plurality of pixels consisting of a target pixel and every pixel in a predetermined range near the target pixel, as a brightness of the target pixel.

Figure 9:
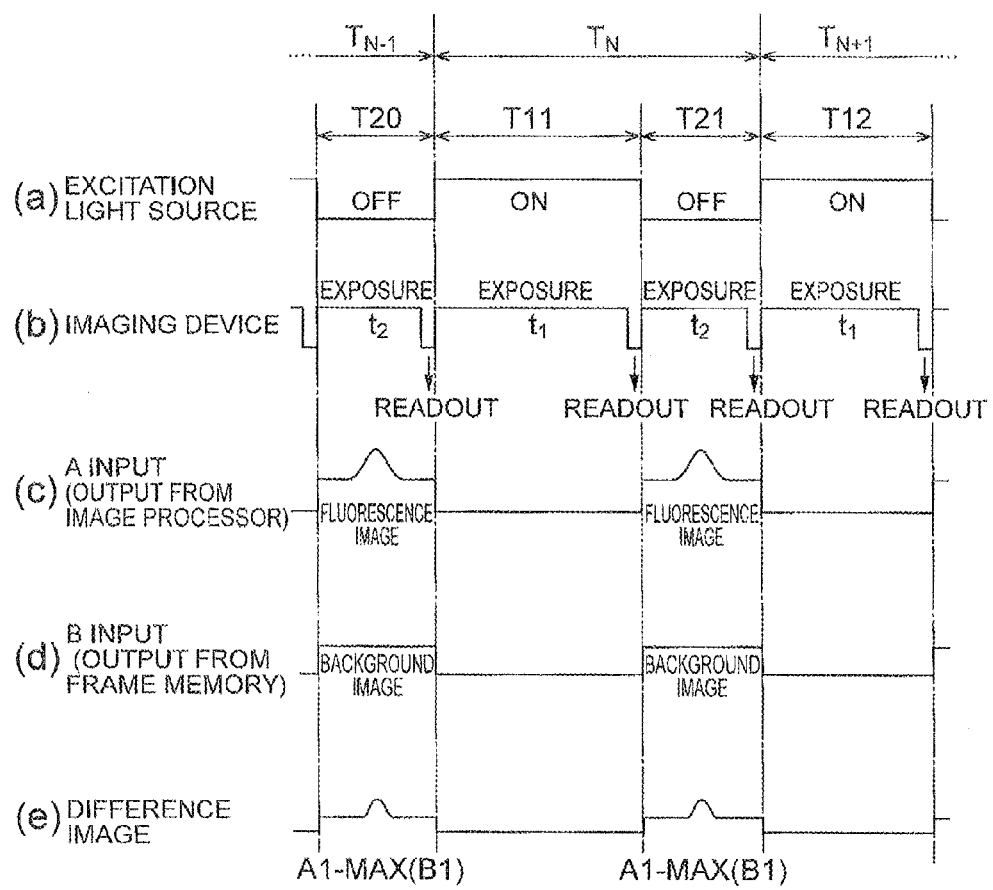
FIG. 9 is a timing chart showing the fluorescence viewing method to be executed in the fluorescence viewing device shown in FIG. 8.

FIG. 9 is a timing chart showing the fluorescence viewing method to be executed in the fluorescence viewing device shown in FIG. 8. In the example shown in the same drawing, the fluorescence image acquired in the image acquisition period T111 is fed through the brightness correction based on the first correction value in the image processing unit 13, to the A1 input terminal of the difference arithmetic unit 15 in the image acquisition period 121. The background image acquired in the image acquisition period T20 of the immediately preceding frame acquisition period $T_{N+1}$ is fed through the brightness correction based on the second correction value in the image processing unit 13, to the frame memory 14 in the image acquisition period T11; and, in the image acquisition period T21, the background image thus corrected is then processed by the maximum filter process in the MAX/MIN filter 31 and thereafter fed to the B1 input terminal of the difference arithmetic unit 15. Then, an A1−MAX(B1) operation to calculate the difference between the fluorescence image at the A1 input and the background image at the B1 input is executed in the image acquisition period T21 to generate the difference image as extraction of fluorescence.

In this fluorescence viewing device 1C as described above, the exposure time of the fluorescence image acquisition period and the exposure time of the background image acquisition period are also different from each other. When the exposure time of the fluorescence image acquisition period and the exposure time of the background image acquisition period are made asymmetric in this manner, the observed images are obtained with good smoothness. Since the ON/OFF durations of the excitation light are also asymmetric according to the asymmetry of the exposure times, it is feasible to reduce the user's feeling of strangeness due to the blinking of the excitation light.

In the fluorescence viewing device 1C, the maximum filter process by the MAX/MIN filter 31 is executed for the background image output from the frame memory 14 to the difference arithmetic unit 15. There is a possibility that a false difference image component can be extracted, for example, at a boundary between a light image portion and a dark image portion in the difference image between the first frame image and the second frame image. The false difference image component can also be extracted with the observed object P in motion. In contrast to it, the extraction of the false difference image component can be suppressed by applying the maximum filter process to the background image.

Figure 10:
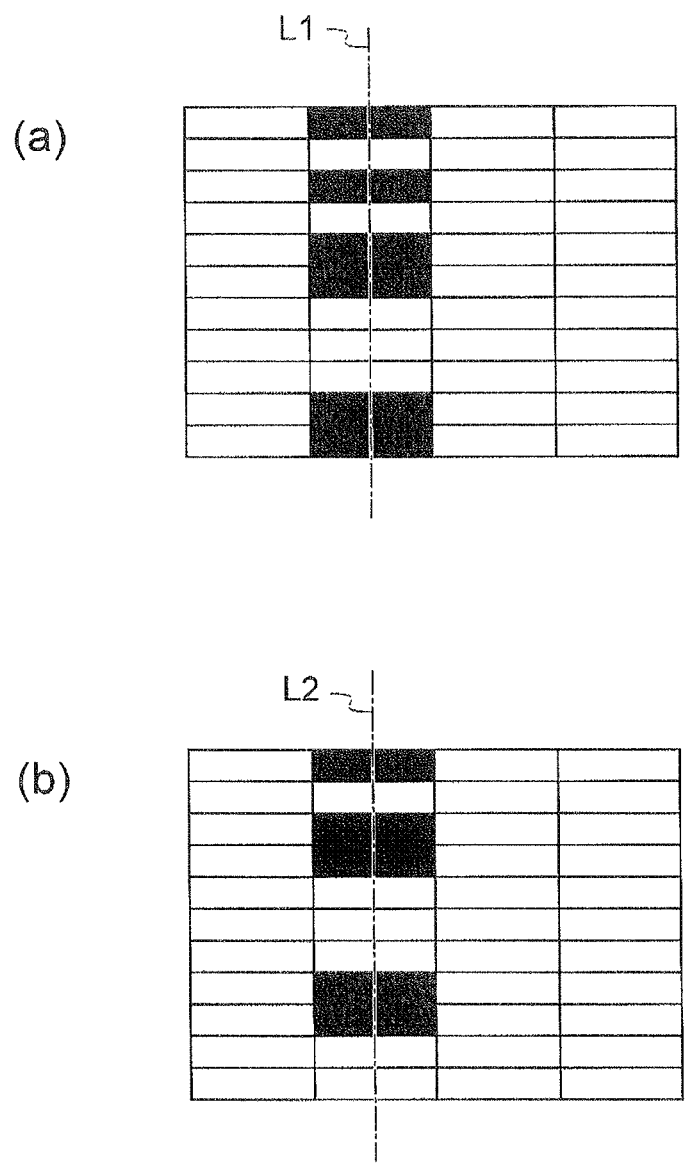
FIG. 10 is a drawing showing an example of images in the fluorescence viewing device shown in FIG. 8, in which (a) is a background image and (b) a fluorescence image.
Figure 11:
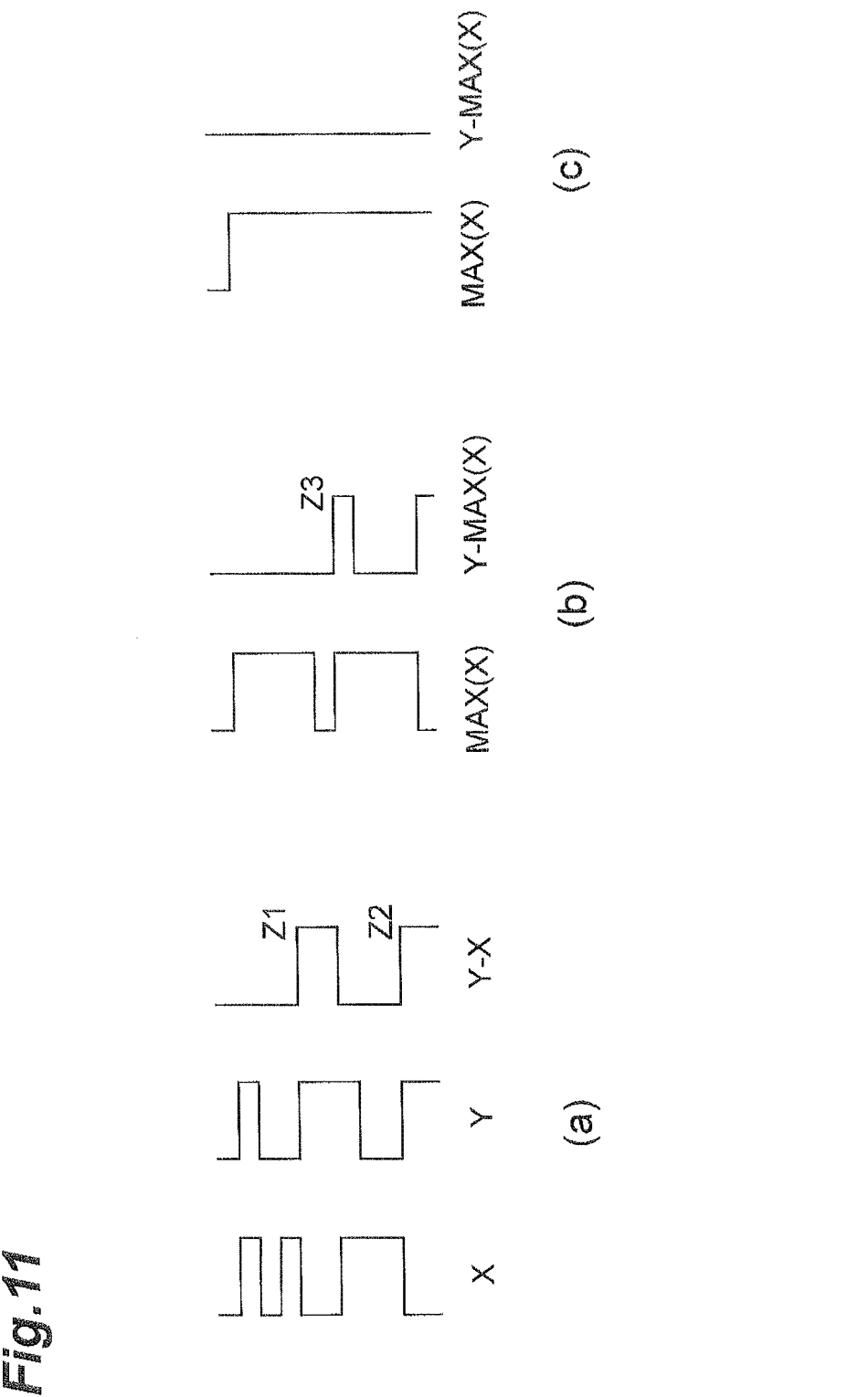
FIG. 11 is a drawing showing how removal of false difference image components is implemented in the example of FIG. 10, in which (a) shows a case of taking an ordinary difference and (b) and (c) cases of implementing a maximum filter process.

The following will describe the effect of suppressing the extraction of the false difference image component by the maximum filter process of the MAX/MIN filter 31. FIG. 10 is a drawing showing an example of images in the fluorescence viewing device shown in FIG. 8, in which (a) is a background image and (b) a fluorescence image. These background image and fluorescence image are images after completion of the brightness correction and show a situation in which the observed object P has moved two pixels upward in a duration from acquisition of the background image to acquisition of the fluorescence image. FIG. 11 is a drawing showing how the removal of the false difference image component is implemented in the example of FIG. 10, in which (a) shows a case of taking an ordinary difference and (b) and (c) cases of implementing the maximum filter process.

In FIG. 11 (a) X indicates a brightness profile along the line L1 in FIG. 10 (a) and Y a brightness profile along the line L2 in FIG. 10 (b). The brightness profile X shows "dark→light→dark→light→dark→dark→light→light-→light→dark→dark" in order from the top pixel in the drawing, whereas the brightness profile Y shows "dark-→light→dark→dark→light→light→light→dark→dark-→light→light" in order from the top in the drawing, as a result of the movement of the observed object P. At this time, the difference image resulting from the Y−X operation should properly have a brightness profile in which all the pixels except for fluorescence signals are "dark," but there appear false difference image components Z1, Z2 at the pixels being "light" in the brightness profile Y and "dark" in the brightness profile X.

For these false difference image components, FIG. 11 (b) shows the case where the maximum filter process is implemented with the number of pixels for the filter process being n=2, and the brightness of the target pixel is defined as a maximum brightness between two pixels consisting of the target pixel and one pixel temporally preceding thereto in the vertical direction. Furthermore, FIG. 11 (c) shows the case where the maximum filter process is implemented with the number of pixels for the filter process being n=3, and the brightness of the target pixel is defined as a maximum brightness among three pixels consisting of the target pixel and two pixels temporally preceding thereto in the vertical direction.

In the maximum filter process with n=2, as shown in FIG. 11 (b), the brightness profile MAX(X) of the background image indicates "dark→light→light→light→light→dark-→light→light→light→light→dark," as a result of replacement of the brightness of the immediately preceding pixel from "dark" to "light." It results in removing the false difference image components Z1, Z2 in the difference image resulting from the Y−MAX(X) operation. On the other hand, in the difference image resulting from the Y−MAX(X) operation, the sixth pixel in the brightness profile MAX(X) is still "dark" and thus there appears a false difference image component Z3.

In the maximum filter process with n=3 in contrast to the above, as shown in FIG. 11 (c), the brightness profile MAX(X) of the background image indicates "dark→light-→light→light→light→light→light→light→light→light-→light," as a result of replacement of the brightness of the second and first preceding pixels from "dark" to "light." It results in removing all the false difference image components in the difference image resulting from the Y−MAX(X) operation.

Figure 12:
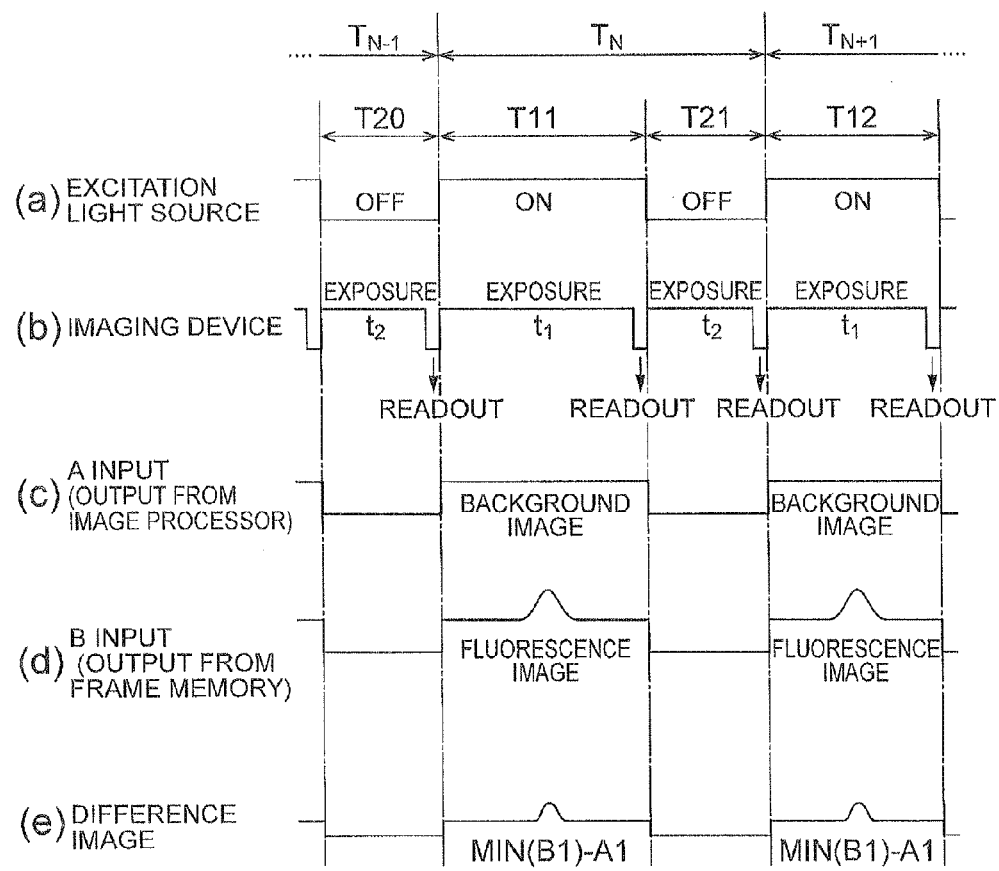
FIG. 12 is a timing chart showing a modification example of the fluorescence viewing method to be executed in the fluorescence viewing device shown in FIG. 8.

FIG. 12 is a timing chart showing a modification example of the fluorescence viewing method to be executed in the fluorescence viewing device shown in FIG. 8. In the example shown in the same drawing, the fluorescence image acquired in the image acquisition period T11 is fed through the brightness correction based on the first correction value in the image processing unit 13, to the frame memory 14 in the image acquisition period T21. The fluorescence image fed into the frame memory 14 is then processed by the minimum filter process in the MAX/MIN filter 31 in the image acquisition period T12 and thereafter fed to the B1 input terminal of the difference arithmetic unit 15. Furthermore, the background image acquired in the image acquisition period T21 is fed through the brightness correction based on the second correction value in the image processing unit 13 to the A1 input terminal of the difference arithmetic unit 15, in the image acquisition period T12. Then, a MIN(B1)−A1 operation to calculate the difference between the fluorescence image at the B1 input and the background image at the A1 input is executed in the image acquisition period T12 to generate the difference image as extraction of fluorescence.

Figure 14:
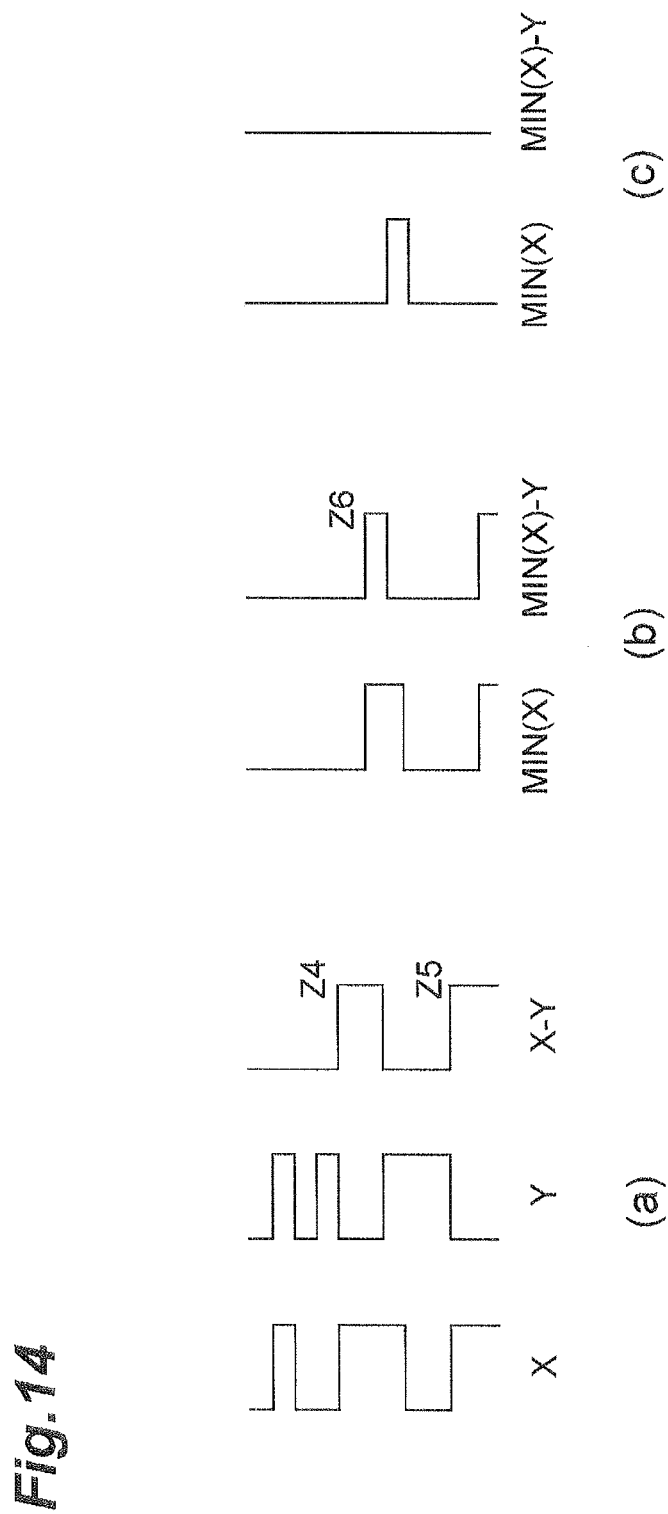
FIG. 14 is a drawing showing how the removal of the false difference image components is implemented in the example of FIG. 13, in which (a) shows a case of taking an ordinary difference and (b) and (c) cases of implementing the minimum filter process.

The following will describe the effect of suppressing the extraction of the false difference image component by the minimum filter process of the MAX/MIN filter 31. FIG. 13 is a drawing showing an example of images in the fluorescence viewing device shown in FIG. 8, in which (a) is a fluorescence image and (b) a background image. These fluorescence image and background image are images after completion of the brightness correction and show a situation in which the observed object P has moved two pixels downward in a duration from acquisition of the fluorescence image to acquisition of the background image. FIG. 14 is a drawing showing how the removal of the false difference image component is implemented in the example of FIG. 13, in which (a) shows a case of taking an ordinary difference and (b) and (c) cases of implementing the minimum filter process.

In FIG. 14 (a) X indicates a brightness profile along the line L3 in FIG. 13 (a) and Y a brightness profile along the line LA in FIG. 13 (b). The brightness profile X shows "dark→light→dark→dark→light→light→light→dark-→dark→light→light" in order from the top pixel in the drawing, whereas the brightness profile Y shows "dark-→light→dark→light→dark→dark→light→light→light-→dark→dark" in order from the top in the drawing, as a result of the movement of the observed object P. At this time, in the difference image resulting from the X−Y operation there appear false difference image components Z4, Z5 at the pixels being "light" in the brightness profile X and "dark" in the brightness profile Y.

For these false difference image components, FIG. 14 (b) shows the case where the minimum filter process is implemented with the number of pixels for the filter process being n=2, and the brightness of the target pixel is defined as a minimum brightness between two pixels consisting of the target pixel and one pixel temporally preceding thereto in the vertical direction. Furthermore, FIG. 14 (c) shows the case where the minimum filter process is implemented with the number of pixels for the filter process being n=3, and the brightness of the target pixel is defined as a minimum brightness among three pixels consisting of the target pixel and two pixels temporally preceding thereto in the vertical direction.

In the minimum filter process with n=2, as shown in FIG. 14 (b), the brightness profile MIN(X) of the fluorescence image indicates "dark→dark→dark→dark→dark→light-→light→dark→dark→dark→light," as a result of replacement of the brightness of the immediately preceding pixel from "light" to "dark." It results in removing the false difference image components Z4, Z5 in the difference image resulting from the MIN(X)−Y operation. On the other hand, in the difference image resulting from the MIN(X)−Y operation, the sixth and seventh pixels in the brightness profile MIN(X) are still "light" and thus there appears a false difference image component Z6.

In the minimum filter process with n=3 in contrast to the above, as shown in FIG. 14 (c), the brightness profile MIN(X) of the fluorescence image indicates "dark→dark-→dark→dark→dark→dark→light→dark→dark→dark-→dark," as a result of replacement of the brightness of the second and first preceding pixels from "light" to "dark." It results in removing all the false difference image components in the difference image resulting from the MIN(X)−Y operation.

It is also possible to adopt a combination of the maximum filter process and minimum filter process described above. FIG. 15 is a timing chart showing another modification example of the fluorescence viewing method to be executed in the fluorescence viewing device shown in FIG. 8. In the example shown in the same drawing, the fluorescence image acquired in the image acquisition period T11 is fed through the brightness correction based on the first correction value in the image processing unit 13, to the frame memory 14 and to the A1 input terminal of the difference arithmetic unit 15 in the image acquisition period T21. Furthermore, the background image acquired in the image acquisition period T20 is fed through the brightness correction based on the second correction value in the image processing unit 13 and processed by the maximum filter process in the MAX/MIN filter 31 and thereafter fed to the B1 input terminal of the difference arithmetic unit 15, in the image acquisition period T21. Then, an A1−MAX(B1) operation to calculate the difference between the fluorescence image at the A1 input and the background image at the B1 input is executed in the image acquisition period T21 to generate the difference image as extraction of fluorescence.

On the other hand, the fluorescence image fed into the frame memory 14 is then processed by the minimum filter process in the MAX/MIN filter 31 in the image acquisition period T12 and thereafter fed to the B1 input terminal of the difference arithmetic unit 15. Furthermore, the background image acquired in the image acquisition period T21 is fed through the brightness correction based on the second correction value in the image processing unit 13 to the A1 input terminal of the difference arithmetic unit 15 and to the frame memory 14, in the image acquisition period T12. Then, a MIN(B1)−A1 operation to calculate the difference between the fluorescence image at the B1 input and the background image at the A1 input is executed in the image acquisition period T12 to generate the difference image as extraction of fluorescence.

In the maximum filter process and minimum filter process in the MAX/MIN filter 31, as the number n of pixels near the target pixel to which the filter process is applied is set to a larger value, the removal performance of the false difference image component can be more improved. On the other hand, as the number n of pixels is set larger, there may arise a problem of enlargement of circuit scale to execute the filter process. Execution of the filter process with a large number n of pixels also has an effect of decreasing the difference image per se, for example.

In view of the foregoing points, the number n of pixels near the target pixel in the maximum filter process and minimum filter process is preferably set to an integer of not less than 3 and not more than 50. It is also possible to adopt a configuration wherein the filter process is implemented using pixels temporally subsequent in the vertical direction to the target pixel, depending upon the filter process circuit, the configuration of the memory, and so on. Furthermore, it is also possible to adopt a configuration wherein the same MAX/MIN filter is applied in the horizontal direction, or, a configuration wherein the MAX/MIN filter is applied in combination of the vertical direction and the horizontal direction.

REFERENCE SIGNS LIST 1A to 1C fluorescence viewing devices; 11 excitation light source (excitation light supply means); 12 imaging device (imaging means); 13 image processing unit (image processing means); 14 frame memory (image storage means); 15 difference arithmetic unit (difference image generation means); 21 white light source (white light supply means); 22 imaging device (imaging means); 23 superimposition arithmetic unit (superimposed image generation means); 31 MAX/MIN filter (filter processing means); P observed object.

The invention claimed is:
1. An apparatus for observing a fluorescence image of an observed object, comprising:
  an excitation light source configured to output excitation light and is capable of implement ON/OFF switching of output of the excitation light;
  an image sensor of a progressive readout type and configured to capture an image of the observed object and alternately output a first frame image and a second frame image in a time series;

an image storage configured to store the first frame image or the second frame image output from the image sensor;

a difference image generator configured to take a difference between one of the first frame image and the second frame image output from the image sensor and the other of the first frame image and the second frame image stored in the image storage to generate a difference image, wherein the excitation light source outputs the excitation light during either the first image capturing period or the second image capturing period in a fluorescence image capturing period and does not output the other period in a background image capturing period, and wherein in the image sensor, an exposure time of the fluorescence image capturing period and an exposure time of the background image capturing period are different from each other; and image processor configured to process correction for a brightness of the fluorescence image and a brightness of the background image, based on a ratio of the exposure time of the fluorescence image capturing period and the exposure time of the background image capturing period.

2. The apparatus according to claim 1, wherein the image processor executes a first correction to correct the brightness of the fluorescence image with use of a first correction value and a second correction to correct the brightness of the background image based on a second correction value, in synchronization with the switching of the output of the excitation light.

3. The apparatus according to claim 1, wherein the excitation light source implements the switching of the output of the excitation light so that the fluorescence image capturing period is longer than the background image capturing period.

4. The apparatus according to claim 1, wherein the exposure time of the background image capturing period or the exposure time of the fluorescence image capturing period is set less than 30 msec.

5. The apparatus according to claim 1, wherein a total time of the fluorescence image capturing period and the background image capturing period is set equal to or less than 60 msec.

6. The apparatus according to claim 1, further comprising:
a white light source configured to output white light;
a second image sensor configured to capture a color image of the observed object; and
a superimposed image generator configured to superimpose the difference image on the color image.

7. The apparatus according to claim 1, further comprising:
a filter configured to perform with respect to the fluorescence image or the background image output from the image storage to the difference image generator and for a brightness of each pixel included in these images, a maximum filter process to define a maximum brightness among a plurality of pixels consisting of a target pixel and every pixel within a predetermined range near the target pixel, as a brightness of the target pixel, or, a minimum filter process to define a minimum brightness among a plurality of pixels consisting of a target pixel and every pixel within a predetermined range near the target pixel, as a brightness of the target pixel.

8. A method for observing a fluorescence image of an observed object, comprising:
irradiating the observed object with excitation light output from an excitation light source in a fluorescence image capturing period;
capturing an fluorescence image of the observed object and outputting a first frame image data by an image sensor of a progressive readout type;
storing the first frame image data in an image storage;
stopping the irradiation of the excitation light in the background image capturing period;
capturing a background image of the observed object and outputting a second frame image data by the image sensor;
taking a difference between the first frame data stored in the image storage and the second frame data output from the image sensor;
wherein an exposure time of the fluorescence image capturing period and an exposure time of the background image capturing period are made different from each other; and
correcting a brightness of the fluorescence image and a brightness of the background image, based on a ratio of the exposure time of the fluorescence image capturing period and the exposure time of the background image capturing period.

9. The method according to claim 8, further comprising:
storing the second frame image data output from the image sensor in the image storage;
irradiating the observed object with the excitation light again;
capturing a second fluorescence image of the observed object and outputting a third frame image data;
taking a difference between the second frame data stored in the image storage and the third frame data output from the image sensor.

10. The method according to claim 8, wherein the fluorescence image capturing period is longer than the background image capturing period.

* * * * *